United States Patent
Calzaferri et al.

(10) Patent No.: US 9,724,433 B2
(45) Date of Patent: Aug. 8, 2017

(54) LOCAL J-COUPLING DYE-ZEOLITE ANTENNA COMPOSITE MATERIALS

(71) Applicants: Universität Zürich, Zürich (CH); Gion Calzaferri, Bremgarten b. Bern (CH); Andreas Kunzmann, Staufen (CH)

(72) Inventors: Gion Calzaferri, Bremgarten b. Bern (CH); Andreas Kunzmann, Staufen (CH); Dominik Bruehwiler, Berikon (CH)

(73) Assignees: Gion Calzaferri, Bremgarten b. Bern (CH); Andreas Kunzmann, Staufen (CH); Unversität Zürich, Zürich (CH)

( * ) Notice: Subject to any disclaimer, the term of this patent is extended or adjusted under 35 U.S.C. 154(b) by 153 days.

(21) Appl. No.: 14/360,877

(22) PCT Filed: Dec. 10, 2012

(86) PCT No.: PCT/EP2012/074951
§ 371 (c)(1),
(2) Date: May 27, 2014

(87) PCT Pub. No.: WO2013/087568
PCT Pub. Date: Jun. 20, 2013

(65) Prior Publication Data
US 2014/0328761 A1    Nov. 6, 2014

(30) Foreign Application Priority Data
Dec. 12, 2011    (EP) ..................................... 11193051

(51) Int. Cl.
*A61K 9/00*    (2006.01)
*A61K 49/00*    (2006.01)
(Continued)

(52) U.S. Cl.
CPC .......... *A61K 49/0013* (2013.01); *C01B 37/04* (2013.01); *C01B 39/02* (2013.01);
(Continued)

(58) Field of Classification Search
CPC .................................................. A61K 49/0013
See application file for complete search history.

(56) References Cited

U.S. PATENT DOCUMENTS

| | | | |
|---|---|---|---|
| 7,655,300 | B2 | 2/2010 | Metz et al. |
| 7,914,702 | B2 | 3/2011 | Calzaferri |
| 2010/0003188 | A1 | 1/2010 | Calzaferri et al. |

FOREIGN PATENT DOCUMENTS

| | | |
|---|---|---|
| CN | 1128455 | 11/2003 |
| EP | 1873202 | 2/2009 |

(Continued)

OTHER PUBLICATIONS

Koeppe et al., "Advanced Photon-Harvesting Concepts for Low-Energy Gap Organic Solar Cells", Solar Energy Materials & Solar Cells 91, Feb. 2007, pp. 986-995, ScienceDirect, Elsevier.

(Continued)

*Primary Examiner* — Paul Dickinson
(74) *Attorney, Agent, or Firm* — Davis & Bujold PLLC; Michael J. Bujold

(57) ABSTRACT

A dye loaded zeolite composite material comprises a plurality of zeolite crystals each having a plurality of straight through uniform channels extending between the proximal face and the distal face and having a channel axis parallel to and a channel width transverse to a longitudinal crystal axis A. Each channel contains a substantially linear arrangement of dye molecules comprising first and second dye molecules having an elongated shape with a longitudinal extension exceeding said channel width and a lateral extension not exceeding said channel width. Each dye molecule consists (Continued)

of a chromophore moiety arranged between a pair of terminal moieties, wherein: the chromophore moieties of the first and second dye molecules are substantially identical, the terminal moieties of the first dye molecules have a lateral extension larger than half of the channel width, the terminal moieties of the second dye molecules have a lateral extension smaller than half of the channel width, the linear arrangement of dye molecules comprises at least one pair of second dye molecules adjacent each other.

13 Claims, 8 Drawing Sheets

(51) Int. Cl.
    C09K 11/06      (2006.01)
    H05B 33/14      (2006.01)
    H05B 33/20      (2006.01)
    C01B 37/04      (2006.01)
    C01B 39/02      (2006.01)
    C09C 1/40       (2006.01)
    C12Q 1/02       (2006.01)
    C12Q 1/70       (2006.01)
    H01G 9/20       (2006.01)
    H01L 51/00      (2006.01)
    H01L 51/50      (2006.01)

(52) U.S. Cl.
    CPC ............... C09C 1/40 (2013.01); C09K 11/06
    (2013.01); C12Q 1/02 (2013.01); C12Q 1/70
    (2013.01); H01G 9/2063 (2013.01); H01L
    51/0072 (2013.01); H05B 33/14 (2013.01);
    H05B 33/20 (2013.01); C09K 2211/1007
    (2013.01); C09K 2211/1011 (2013.01); C09K
    2211/1018 (2013.01); C09K 2211/1022
    (2013.01); C09K 2211/1029 (2013.01); C09K
    2211/1033 (2013.01); C09K 2211/1037
    (2013.01); C09K 2211/1044 (2013.01); C09K
    2211/1088 (2013.01); C09K 2211/1092
    (2013.01); H01L 51/5012 (2013.01)

(56) References Cited

FOREIGN PATENT DOCUMENTS

| EP | 2141122 | 1/2010 |
|----|---------|--------|
| GB | 2461686 | 1/2010 |
| WO | 02/36490 | 5/2002 |
| WO | 2007/012216 | 2/2007 |
| WO | 2008/052603 | 5/2008 |
| WO | 2010/009560 | 1/2010 |

OTHER PUBLICATIONS

Rademacher et al., "Lösliche Perylen-Fluoreszenzfarbstoffe mit hoher Photostabilität", Chem. Ber. 115, pp. 2927-2934, Dec. 1981, Verlag Chemie GmbH, Weinheim.

Calzaferri et al., "Playing with Dye Molecules at the Inner and Outer Surface of Zeolite L", Solid State Sciences 2, 2000, pp. 421-447, Elsevier.

Busby et al., "Interactions of Perylene Bisimide in the One-Dimensional Channels of Zeolite L", The Journal of Physical Chemistry, Mar. 4, 2011, pp. 5974-5988, 115, American Chemical Society.

Calzaferri et al., "Designing Dye-Nanochannel Antenna Hybrid Materials for Light Harvesting, Transport and Trapping", ChemPhysChem, Feb. 15, 2011, 12, pp. 580-594, Wiley-VCH Verlag GmbH & Co. KGaA, Weinheim.

Koide et al., "Development of an Si-Rhodamine-Based Far-Red to Near-Infared . . . ", Journal of the American Chemical Society, Mar. 28, 2011, 133, pp. 5680-5682, American Chemical Society.

Holtrup et al., "Terrylenimides: New NIR Fluorescent Dyes", Chem. Eur. J. 1997, 3, No. 2, pp. 219-225, May 8, 1996, VCH Verlagsgesellschaft mbH, Weinheim.

Calzaferri et al., "Mimicking the Antenna System of Green Plants", Photochemical & Photobiological Sciences, Aug. 2008, vol. 7, No. 8, pp. 869-992, Switzerland.

Bruehwiler et al., "Nanochannels for Supramolecular Organization of Luminescent Guests", J. Mater. Chem., Jul. 14, 2009, 19, pp. 8040-8067, Switzerland.

Lopez-Duarte et al., "On the Significance of the Anchoring Group in the Design . . . ", Chem. Eur. J. 2011, 17, pp. 1855-1862, Nov. 24, 2010, Wiley-VCH Verlag GmbH & Co. KGaA, Weinheim.

Busby et al., "Time, Space, and Spectrally Resolved Studies on J-Aggregate Interactions in Zeolite L Nanochannels", JACS Articles, Jul. 29, 2008, J. Am. Chem. Soc. 2008, 130, pp. 10970-10976, American Chemical Society.

Weissleder, "A Clearer Vision for In Vivo Imaging", Nature Biotechnology, Apr. 2001, vol. 19, pp. 316-317, Nature Publishing Group.

Wang et al., "Orienting Zeolite L Microcrystals with a Functional Linker", Angew. Chem. Int. Ed. 2010, 49, pp. 1434-1438, Wiley-VCH Verlag GmbH & Co. KGaA, Weinheim.

Li et al., "Surface Modification and Functionalization of Microporous Hybrid Material for Luminescence Sensing", Chem. Eur. J. 2010, 16, pp. 2125-2130, Jan. 11, 2010, Wiley-VCH Verlag GmbH & Co. KGaA, Weinheim.

Pauchard et al., "Dye-Loaded Zeolite L Sandwiches as Artificial Antenna Systems for Light Transport", Chem. Eur. J. 2000, 6, No. 18, pp. 3456-3470, Mar. 23, 2000, Wiley-VCH Verlag GmbH & Co. KGaA, Weinheim.

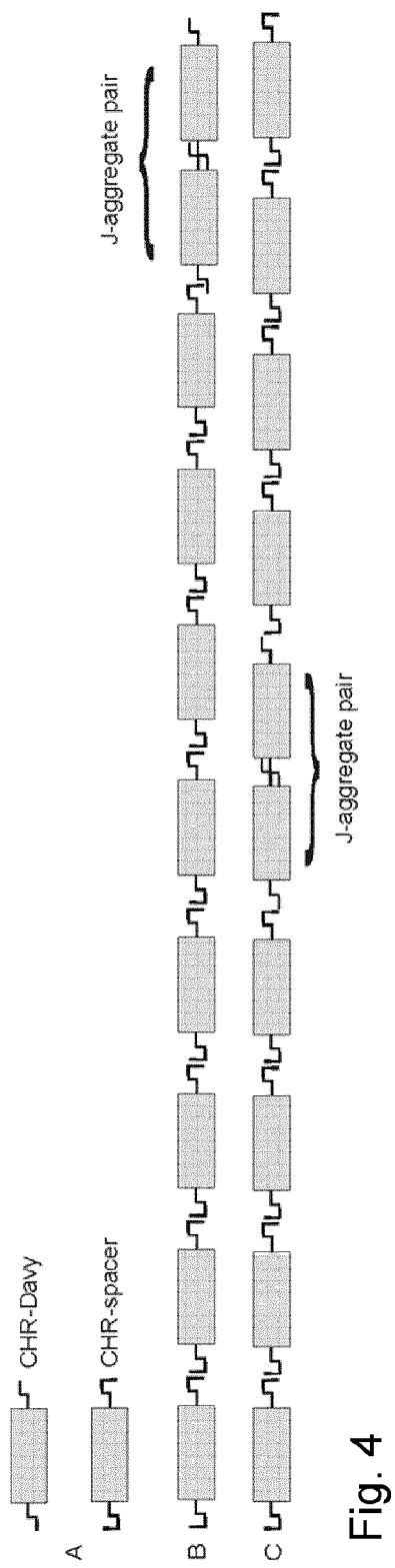
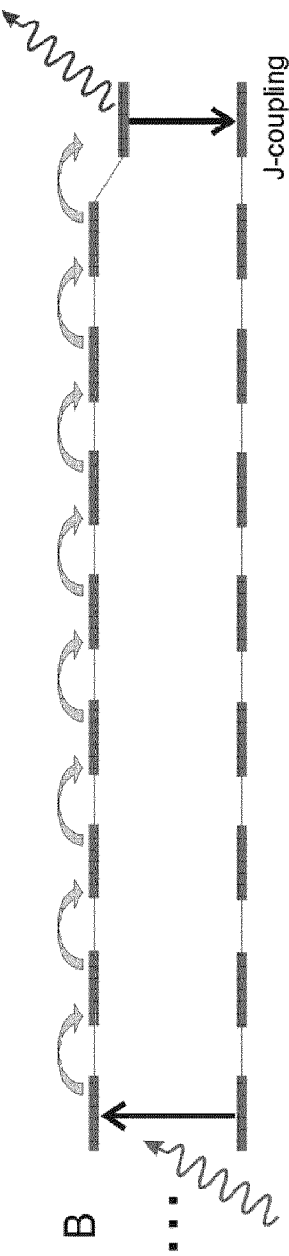
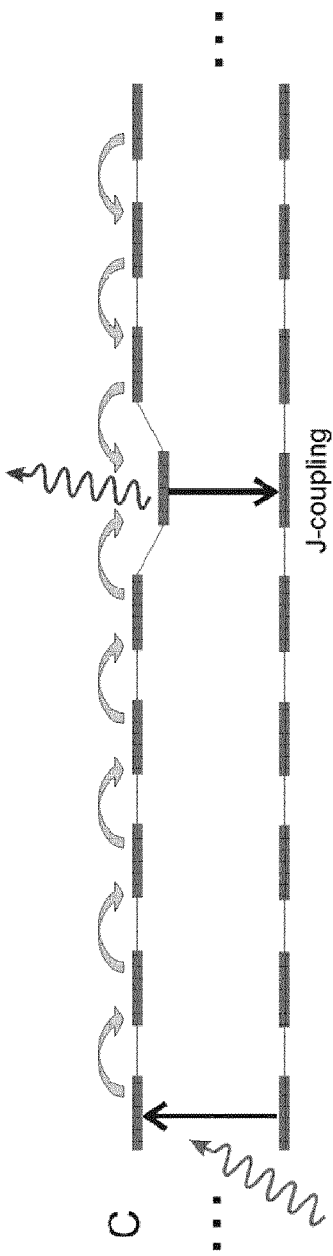
Fig. 4
Fig. 5

LOCAL J-COUPLING DYE-ZEOLITE ANTENNA COMPOSITE MATERIALS

FIELD OF THE INVENTION

The present invention relates to the technical field of optical materials and devices. In particular, the invention relates to dye-zeolite composite materials; the invention further relates to a pigment material, a luminescent optical device, a luminescence concentrator, an inverted luminescence concentrator, a color change medium, an optical sensor device, a light emitting device and a photon harvesting device, imaging of biological cells or viruses and for use in in-vitro and in-vivo diagnostics, all the aforesaid comprising a dye loaded zeolite composite material.

BACKGROUND OF THE INVENTION

Assemblies, polymers, crystals, and biological structures bearing nanochannels have been studied for many decades. Examples of nanochannel materials are zeolites, zeotypes, cyclodextrins, urea based assemblies, mesoporous silica materials, collagens, metal organic frameworks, as well as organic-, carbon- and metaloxide-channels. All have been investigated to some extent as hosts for molecules, complexes, ions, or clusters. One dimensional (1D) nanochannels have special properties which have recently attracted considerable attention. We distinguish between several types of 1D channels: single file, ordered assemblies, amorphous, "semicrystalline", and crystalline. A common feature of 1D channels is that they have only 2 entrances. Channels can therefore be open on both sides, plugged on one side, or plugged on both sides. This plugging can be isolating or it can be partial, allowing electrons, protons, or small molecules to pass, but blocking larger objects. Zeolites with hexagonal structures are interesting materials bearing 1D channels and among them zeolite L (ZL) is especially important for preparing strongly luminescent organic-inorganic dye-zeolite hybrid materials. (U.S. Pat. No. 7,914,702; G. Calzaferri et al.: Mimicking the Antenna System of Green Plants, Photochem. Photobiol. Sci., 2008, 7, 879; D. Brühwiler et al.: Nanochannels for Supramolecular Organization of Luminescent Guests, J. Mater. Chem., 2009, 19, 8040; EP 18732002, U.S. Pat. No. 7,655,300; WO 2008/052603, PCT/EP2007/005811, China 1128455; G. Calzaferri et al.: Designing Dye-Nanochannel Antenna Hybrid Materials for Light Harvesting, Transport and Trapping, ChemPhysChem, 2011, 12, 580.)

Classical zeolites are aluminosilicate crystalline minerals which have a microporous structure, according to IUPAC nomenclature, but which are actually nanoporous. Their "open" structure can accommodate a wide variety of molecules, ions and clusters. Zeolites are therefore often referred to as "molecular sieves". The term molecular sieve refers to a particular property of zeolites, i.e. their ability to selectively sort molecules based primarily on a size exclusion process. The size exclusion process is due to the highly regular pore structure of molecular dimensions. The maximum size of a molecular or ionic substance that can enter the pores of the zeolite is controlled by the diameters of the channels within the zeolite. These channels are conventionally defined by the ring size of the aperture, where, for example, the term "12-ring" refers to a closed loop that is built from 12 tetrahedrally coordinated silicon or aluminum atoms and 12 oxygen atoms. ZL crystals, which can be prepared in a size range of 30 nm up to about 10000 nm and with different morphology such as elongated, barrel type and disc shaped crystals, have hexagonal structure. A ZL crystal of 600 nm diameter consists of roughly 100000 strictly parallel channels, with a channel opening diameter of 0.71 nm and a largest inner diameter of 1.24 nm, which can be filled e.g. with dye molecules. The ZeoFRET® (Zeo=zeolite, FRET=Förster Resonance Energy Transfer) nanochannel-materials are highly organized dye-zeolite inclusion compounds with photonic antenna function. After absorption of the incident light by high local concentrations of dye molecules, the energy is transported by FRET to an acceptor A. High donor-to-acceptor (D:A) ratios and multi-donor systems are promising as active species in luminescence concentrators (LC) and luminescence solar concentrators (LSC) (WO 2010/009560) High D:A ratios thereby open possibilities to reduce self-absorption, also known as inner filter effect, while maintaining efficient light-harvesting. We have synthesized ZeoFRET® materials according to this concept with different D:A ratios. In one example, one channel of ZL contained approximately 150 donor dyes and on average 1.5 acceptor dyes at each channel end (G. Calzaferri et al.: Designing Dye-Nanochannel Antenna Hybrid Materials for Light Harvesting, Transport and Trapping, ChemPhysChem, 2011, 12, 580.)

The packing of the molecules inside the channels influences the materials properties. So called H-dimers can be formed if the molecules are sufficiently small. This patent focuses on molecules too large and channels too narrow for allowing this. The molecules may, however, still be of a size and shape so that they can come close enough for allowing sufficiently strong coupling of their electronic transition dipole moments thereby increasing the importance of excimer and exciton states. Signature of Davydov coupling (herein called J-coupling) has therefore been observed, studied, and reported. J-coupling strength, which we abbreviate as $\beta_c$, can be calculated as follows:

$$\beta_c = AD \cdot f \cdot \kappa / (\Delta E \cdot R^3 \cdot n^2)$$

The value of the constant AD is equal to $1.615 \cdot 10^{-18}$ m² cm⁻¹ if we express $\beta_c$ in cm⁻¹. The magnitude of interactions $\beta_c$ caused by exciton coupling, and hence the resulting splitting of the levels, depends on the oscillator strength f, the relative Orientation $\kappa$ of two neighboring electronic transition moments, and the distance R between the interacting electronic transition dipole moments. The expression for $\kappa$ can be simplified in the present case as $\kappa = 1 - 3\cos^2(\theta)$, where $\theta$ is the angle between two adjacent electronic transition dipole moments with values close to 0° and always smaller than 40°. A typical orientation of the electronic transition moments of the chromophores for the materials of interest is shown in FIG. 1 as double arrows. This distance is very often equal to the distance between the centers of the involved chromophores. $\beta_c$ further depends on the electronic excitation energy $\Delta E$, and on the refractive index n of the environment. (G. Calzaferri et al.: Mimicking the Antenna System of Green Plants, Photochem. Photobiol. Sci., 2008, 7, 879; M. Busby et al.: Time, Space and Spectrally Resolved Studies on J-Aggregate Interactions in Zeolite-L Nanochannels, J. Am. Chem. Soc., 2008, 130, 10970; M. Busby et al.: Interactions of Perylene Bisimide in the One Dimensional Channels of Zeolite L, J. Phys. Chem. C, 2011, 115, 5974; UK 0812218.6, US 2010/0003188).

High D:A ratios are needed for efficient light-harvesting of the ZeoFRET® materials, the technical applications of which have been described in the references given above. The donors D absorb light at shorter wavelengths than the acceptors A. In order to shift the light absorption of the material to longer wavelengths, donors must be chosen such that they absorb at longer wavelength which means that the acceptor absorption wavelength must be shifted accordingly. This is not an important problem as long as the absorption wavelength threshold of the ZeoFRET® is not larger than 550 nm or 600 nm. It causes, however, practical problems at longer wavelengths which increase the more the absorption wavelength is shifted to large values such as 700 nm, 750 nm, 800 nm, 850 nm, 900 nm, or even 950 nm. One of the reasons for these problems is the limited number of molecules available that can act as good acceptors, that are sufficiently stable, that have large luminescence quantum yield, and that can be inserted into the channels of the host material used for the synthesis of ZeoFRET® in a way that a photochemically and thermally stable ZeoFRET® material with large luminescence output can be synthesized. An important reason for near infrared (NIR) absorption and emission is the fact that skin and muscles are sufficiently transparent in the wavelength range of 650-900 nm, which is known as (optical) therapeutic window for e.g. a detection or action depth of 500 micrometer up to a few cm (R. Weissleder: A Clearer Vision for in vivo Imaging; Progress Continues in the Development of Smaller, More Penetrable Probes for Biological Imaging, Nat. Biotechnol., 2011, 19, 316.)

SUMMARY OF THE INVENTION

Accordingly, it is an object of the present invention to overcome the above discussed shortcomings and disadvantages associated with ZeoFRET® and other dye-zeolite composite materials and any devices that have so far been described.

ZeoFRET® nanochannel materials are highly organized dye-zeolite inclusion compounds with photonic antenna function. After absorption of the incident light by high local concentrations of dye molecules, the energy is transported by FRET to an acceptor A. Large donor-to-acceptor (D:A) ratios, typically above 20, and multi-donor systems are promising as active species in luminescence solar concentrators. Large D:A ratios thereby open possibilities to reduce self-absorption while maintaining or enhancing efficient light-harvesting.

In particular, it is an objective of this invention to provide a material that is suitable for a wide variety of applications and that shows extended and broadband absorption wavelength range and, hence, improved light-harvesting, being easier to synthesize as compared to known dye loaded zeolite composite materials. Further objects of this invention are to provide pigment materials showing improved performance in a luminescence optical device, in luminescence concentrators, in luminescence solar concentrators, in inverted luminescence concentrators (iLC), in color change media, to provide improved performance in imaging of biological cells or viruses and for use in in-vitro and in-vivo diagnostics.

According to one aspect of the invention (claim 1), a dye loaded zeolite composite material comprises a plurality of zeolite crystals, each one of said crystals having a proximal face and a distal face opposed therefrom and substantially parallel to said proximal face, each one of said crystals having a plurality of straight through uniform channels extending between the proximal face and the distal face and having a channel axis parallel to and a channel width transverse to a longitudinal crystal axis A, each channel having a proximal channel end located at the proximal face and a distal channel end located at the distal face, said channels containing a substantially linear arrangement of dye molecules, each one of said dye molecules having an elongated shape with a longitudinal extension exceeding said channel width and a lateral extension not exceeding said channel width, said linear arrangement of dye molecules comprising first dye molecules and second dye molecules, each one of said first and second dye molecules consisting of a chromophore moiety arranged between a pair of terminal moieties, wherein the chromophore moieties of said first dye molecules and of said second dye molecules are substantially identical, the terminal moieties of said first dye molecules have a lateral extension larger than half of said channel width, the terminal moieties of said second dye molecules have a lateral extension smaller than half of said channel width, said linear arrangement of dye molecules comprises at least one pair of second dye molecules adjacent each other.

In the present context, "substantially identical" chromophore moieties shall be understood to encompass minor changes that arise when two identical chromophore moieties are provided with different terminal moieties, which, however, do not interact strongly with the chrompohore moiety.

The "lateral extension" of a molecular moiety shall be understood as the largest extension in any direction perpendicular to a longitudinal axis of the respective dye molecule.

By virtue of the fact that the terminal moieties of the first dye molecules have a lateral extension larger than half channel width, the terminal moieties effectively act as spacer elements because an overlap of the terminal moieties of two adjacent first dye molecules is prevented due to the lateral limitation by the channel boundary.

In contrast, the terminal moieties of the second dye molecules have a lateral extension smaller than the channel width, thus allowing for overlap of the terminal moieties of two adjacent second dye molecules, which effectively means a substantially smaller longitudinal distance between the two respective chromophore moieties.

In one embodiment, the terminal moieties of the first dye molecules are identical (claim 2). In a further embodiment, the terminal moieties of the second dye molecules are identical (claim 3). This results in a simpler overall system, at least conceptually.

Advantageously, the molar ratio of the first dye to the second dye is at least 20 (claim 4); in particular, it may be larger than 30 and, more particularly, larger than 50.

In a further embodiment (claim 5), the linear arrangement of dye molecules further comprises third dye molecules having an electronic excitation energy that is larger than the electronic excitation energy of the first and second dye molecules. These third dye molecules can be employed to absorb shorter wavelength light, which is then transferred to longer wavelength by transfer to the first and second dye molecules.

In a further embodiment (claim 6), the channel ends are provided with closure units. These closure units may be formed by single molecular entities (claim 7), as previously described e.g. in WO 02/36490.

Alternatively, the closure unites may be formed by parts of a closure layer (claim 8), as previously described e.g. in WO 2007/012216. For some applications, it will be advantageous to have the closure layer attached to a solid substrate (claim 9).

According to a further aspect of the invention (claim 10), a method of producing a dye loaded zeolite composite material as defined above comprises the steps of:

a) providing an amount of zeolite crystals, each one of said crystals having a pair of substantially parallel faces, each one of said crystals further having a plurality of straight through uniform channels extending between said two faces and having a channel axis parallel to and a channel width transverse to a longitudinal crystal axis A;

b) either:

loading a first amount of the first dye into the zeolite channels followed by adding thereto a second amount of the second dye, thereby forming a dye loaded zeolite composite material having a terminal acceptor configuration; or else:

loading a first amount of the second dye into the zeolite channels followed by adding thereto a second amount of the first dye, thereby forming a dye loaded zeolite composite material having an internal acceptor configuration.

In the present context, a "terminal acceptor configuration" shall be understood as an arrangement of dye molecules wherein the second dye molecules are positioned at a terminal side of the arrangement. Analogously, an "internal acceptor configuration" shall be understood as an arrangement of dye molecules wherein the second dye molecules are positioned at an internal region of the arrangement.

In one embodiment (claim 11), a step of closing the zeolite channels is performed after loading the same with dye molecules.

Depending on the type of closure to be applied to the channel ends, one may adopt the method of claim 12 or claim 13.

The present invention is based on the observation that J-aggregates can form in the channels of dye loaded ZL and that the reasons for this property is now well understood, as outlined in the background of the invention. Some practical consequences of this observation and understanding have been reported in the patent application UK 0812218.6, US 2010/0003188. This present invention consists of a fundamentally new idea of using this behavior of molecules, depending on their shape, inside of the channels. The J-coupling strength is reduced by a factor of 3.375 if the distance between the two chromophores is enlarged by ⅓, because of its inverse power to the third distance dependence. This distance can be controlled for all dyes that can be inserted into the channels of ZL, either by cation exchange or by insertion from the gas phase, by adding optically inert or almost inert groups. Two perylene molecules with identical chromophore but different end groups can be used as an example. Other examples are two Bodipy or Xanthene or Cyanine or Stilbene molecules with identical chromophore but different end groups.

The invention relies on using the possibility to insert molecules with identical chromophoric unit but with different distance controlling end groups, so that one type of molecule, which we name CHR-Davy, has end groups allowing dense packing, leading to a coupling strength $\beta_c$ of at least 100 cm$^{-1}$. The other type of molecule, called CHR-spacer, possesses end groups that keep the distance between the molecules in the channels so large that the coupling strength $\beta_c$ is smaller than that of CHR-Davy.

Combining the molecules CHR-spacer and CHR-Davy allows to synthesize ZeoFRET® materials with a large light absorption range and large luminescence output by using the J-aggregates built by the CHR-Davy molecules as acceptors which emit at wavelengths where the CHR-spacer molecules do not or only very little absorb light. This new material is called local J-coupling ZeoFRET® material and abbreviated as LJ-ZeoFRET® material. Two configurations can be synthesized, namely the configurations (B) and (C). The local J-coupling situation is realized by adding two CHR-Davy molecules as acceptors at each channel end for the design (B) and by adding two CHR-Davy molecules as acceptors at an arbitrary position in the channels for the design (C). A favorable J-coupling situation can in both cases also be realized by allowing J-coupling between three or in some cases even four CHR-Davy molecules; for most applications some tolerance in the number of coupling CHR-Davy molecules can be allowed. The advantage of option (C) is that it can be realized in a one pot synthesis procedure while a two-step procedure is needed for option (B). The latter, however, allows for better and more precise control of the materials synthesis. Design (B) is needed for devices for which the electronic excitation energy must be transported via FRET to the channel ends, so that it can be transferred to (or interact with) a next object, located at the channel end. This may be necessary or advantageous for sensitized solar cell devices, for light emitting organic diode devices, for sensing devices and for some diagnostic devices. Design (C) is a good option, if out-coupling of the electronic excitation energy by luminescence of the J-aggregate is required, as for example in ZeoFRET® luminescence concentrator, ZeoFRET® luminescence solar concentrator and ZeoFRET® inverted luminescence concentrator devices, for which of course also design (B) can be used. The coupling J-aggregate pair can be covalently linked, if desired. Dye combinations with molecules such as zinc phthalocyanine (ZnPc) molecules that are located at the entrances of the ZL channels are of interest for the sensitization of ZnPc-based solar cells (I. López-Duarte et al.: On the Significance of the Anchoring Group in the Design of Antenna Materials Based on Phthalocyanine Stopcocks and Zeolite L, Chem. Eur. J., 2011, 17, 1855).

Advantages that result from this invention with respect to designs that have been invented or known so far are that the chromophore part of the molecules CHR-spacer and CHR-Davy is identical. The synthesis of the LJ-ZeoFRET® material is greatly simplified which allows producing it at lower cost and opens possibilities for producing materials which otherwise cannot be produced. The optical light absorption range of the molecules can be fully exploited. This is especially important for luminescence solar concentrators but also for other applications. While in a conventional antenna material, where the acceptors are different dyes and the absorption range of the acceptors cannot or only partly be used, there is no such limitation for the LJ-ZeoFRET® materials. Imagine that a chromophore is used which absorbs light at wavelengths shorter than 700 nm. In a conventional ZeoFRET® material an acceptor dye must be found that absorbs at longer wavelength than 700 nm. Only small amounts of acceptor dye can be added, however, since the D:A ratio should be at least 20 in order to avoid self-absorption. This means that the acceptor dye does not contribute significantly to the light absorption of the ZeoFRET®. The difficulty for realizing this step increases with increasing absorption wavelength. This problem can be circumvented by using the LJ-ZeoFRET® materials, because the absorption range of the molecules CHR-spacer and CHR-Davy is structurally the same. Good examples for dyes for which the CHR-spacer and CHR-Davy concept can be realized are perylene, terylene, cyanine, oxazine, bodipy, stilbene, and xanthene dyes.

A typical concept for preparing LJ-ZeoFRET® materials uses two different dyes, one absorbing light at shorter wavelength and the second absorbing light at longer wavelength, a combination of CHR-spacer and CHR-Davy which have the same or nearly the same electronic absorption and luminescence spectra. The light out-coupling is performed by the J-coupling pair. Stability can be maximized by e.g. selectively plugging the channel entrances by means of a cationic polymer. The chemical and mechanical stability can be further improved by covering the individual particles with a silica layer which can be realized by using standard sol-gel chemistry (H. Li et al.: Surface Modification and Functionalization of Microporous Hybrid Material for Luminescence Sensing, Chem. Eur. J., 2010, 16, 2125). This procedure results in non-toxic environmentally friendly materials, independent of the kind of molecules that are in the ZL channels. The hexagonal ZL crystals can be assembled in several ways for realizing optically highly anisotropic layers (Y. Wang et al.: Orienting Zeolite L Microcrystals with a Functional Linker, Angew. Chem. Int. Ed., 2010, 49, 1434).

An important reason for near infrared (NIR) absorption and emission is the fact that skin and muscles are sufficiently transparent in the wavelength range of 650-900 nm, which is known as (optical) therapeutic window for e.g. a detection or action depth of 500 micrometer up to a few cm and that this wavelength range can be better covered with the LJ-ZeoFRET® materials than with any dye-zeolite composite material known so far.

BRIEF DESCRIPTION OF THE FIGURES

FIG. 4. Illustration of the way to control the distance between the chromophoric part of the dyes by adding distance keeping end groups in case of the CHR-spacer dyes and end groups which allow short distances and hence strong J-coupling in case of the CHR-Davy dyes.

FIG. 5. Photophysical principle of the LJ-ZeoFRET® material.

DETAILED DESCRIPTION OF THE INVENTION

Figure 1:
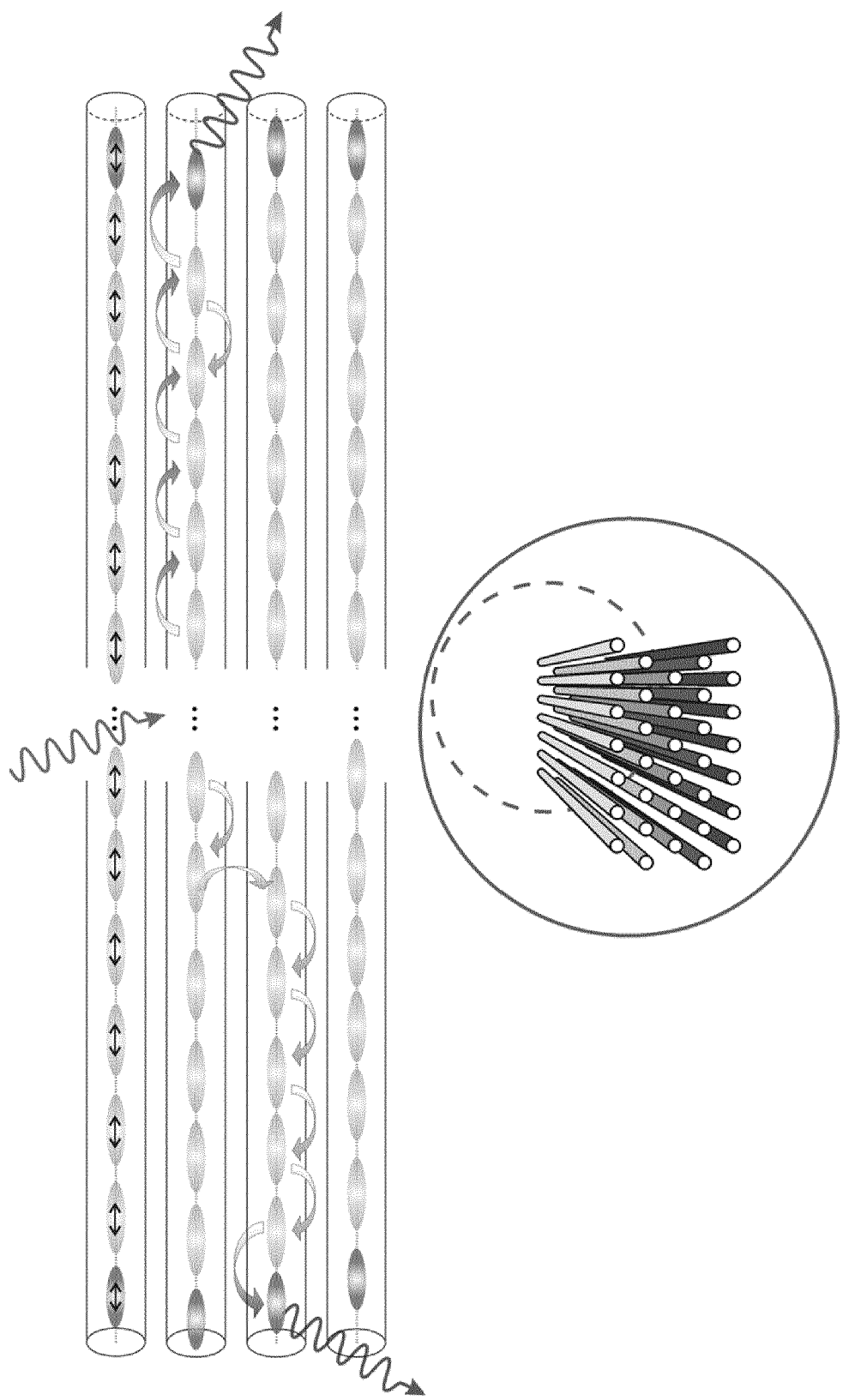
FIG. 1. Schematic view of an artificial photonic antenna representing the structure of a ZeoFRET® particle.

ZeoFRET® materials are highly organized dye-zeolite inclusion composites with photonic antenna function (Zeo=zeolite, FRET=Förster Resonance Energy Transfer). After efficient absorption of the incident light by high local concentrations of dye molecules, the energy is transported by FRET to an acceptor species. The principle is illustrated in FIG. 1 where a schematic view of an artificial photonic antenna representing the structure of a ZeoFRET® particle is shown. The chromophores are embedded in the channels of the host. The light grey dyes act as donor molecules which absorb the incoming light and transport the excitation via FRET to the dark grey acceptors shown at both ends of the channels. A top view of an array of such strictly parallel channels is shown at the bottom of FIG. 1.

The organization of the dye molecules in the nanochannels of the ZL crystals can be extended to the macroscopic scale, leading to systems with high optical anisotropy. The dye components of the ZeoFRET® materials are chosen according to the desired application.

Figure 2:
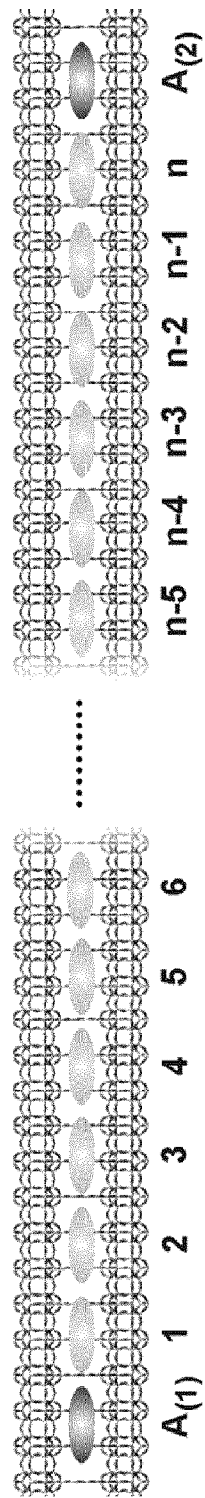
FIG. 2. A nanochannel of ZL containing n donor dyes and one acceptor dye at each channel end.

High donor-to-acceptor (D:A) ratios and multi-donor systems are promising as active species in luminescence solar concentrators. Large D:A ratios, typically above 20, thereby open possibilities to reduce self-absorption while maintaining efficient light-harvesting. An illustration of a ZL channel with a D:A ratio of n:2 is shown in FIG. 2, where we see a nanochannel of ZL containing n donor dyes and one acceptor dye at each channel end. The donor dyes absorb the incoming light and transfer the energy to the acceptor dyes, which subsequently emit light in a wavelength range where the donor molecules do not absorb. A ZL crystal of 600 nm diameter consists of roughly 100000 strictly parallel channels.

We have synthesized ZeoFRET® materials with different D:A ratios according to this concept. In one example, one channel of ZL contained approximately 150 donor dyes and on average 1.5 acceptor dyes at each channel end.

Figure 3:
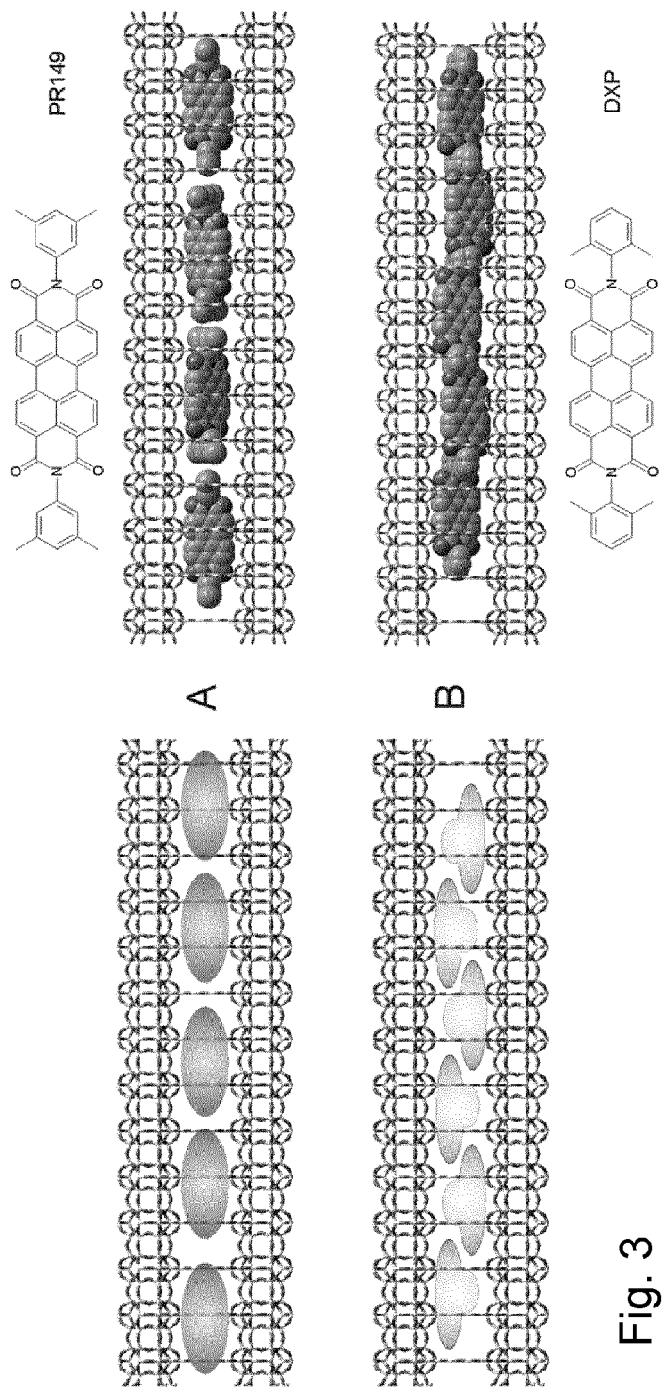
FIG. 3. Orientation and packing of dyes inside of the ZL nanochannels.

The present invention consists of a fundamentally new idea of using the property of dye molecules to undergo J-coupling inside of the channels, the strength of which depends on their properties, especially also on their shape. The J-coupling strength is reduced by a factor of 3.375 if the distance between the two chromophores is enlarged by ⅓, because of its power to the third distance dependence. This distance can be controlled for all dyes that can be inserted into the channels of ZL either by cation exchange or by insertion from the gas phase by adding optically inert or almost inert groups. We illustrate this for the two perylene dyes DXP and PR149 in FIG. 3, where orientation and packing of dyes in the channels are shown. DXP and PR149 are large molecules which align with their long axis parallel to the channel axis because of their size and their shape. (A): Dense packing of the perylene dye PR149. The shape of the dyes is such that dense packing corresponds to the scheme on the left. (B): Dense packing of DXP leads to exciton states. The position of the methyl groups of DXP allows denser packing, so that J-coupling becomes important. While considerable J-coupling of DXP that has been inserted into the channels of ZL is observed, this coupling is so small in case of PR149 that it has not yet been observed. The electronic spectra of both dyes are the same under high dilution, which means that the difference of ortho versus meta substitution of the phenyl groups has no influence on the electronic properties of the "optical electrons" associated with the individual chromophore units of the individual molecules. The difference, however, affects the packing realized inside of the channels, as illustrated in FIG. 3.

The invention consists of using the possibility to insert molecules with identical chromophoric unit but with different distance controlling end groups, so that one type of molecule, which we name CHR-Davy, has end groups allowing dense packing, leading to a coupling strength $\beta_c$ of at least 100 cm$^{-1}$. The other type of molecule, called CHR-spacer, possesses end groups that keep the distance between the molecules in the channels so large that the coupling strength $\beta_c$ is smaller than that of CHR-Davy.

Combining the dyes CHR-spacer and CHR-Davy allows to synthesize LJ-ZeoFRET® materials with a large light absorption range and large luminescence output by using the J-aggregates built by the CHR-Davy dyes as acceptors, which emit at wavelengths where the donor dyes do not or only very little absorb light. FIG. 4 shows two configurations which can be synthesized. FIG. 4(A) illustrates the way to control the distance between the chromophore part of the dyes by adding distance keeping end groups in case of the CHR-spacer dyes and end groups which allow short distances and hence strong J-coupling in case of the CHR-Davy dyes. The chromophore part of CHR-Davy and CHR-spacer is identical. FIG. 4(B) shows a design in which the J-coupling elements are located at the ends of the channel. FIG. 4(C) shows a design in which the J-coupling elements are located at an arbitrary position in the channel. Configurations (B) and (C) explain the local J-coupling situations, realized by adding two CHR-Davy dyes as acceptors at each channel end for the design (B) and by adding two CHR-Davy dyes as acceptors somewhere, i.e. at an arbitrary position, for the situation (C). A favorable J-coupling situation can in both cases also be realized by allowing J-coupling between three or in some cases even four CHR-Davy dyes; for most applications some tolerance in the number of coupling CHR-Davy dyes can be allowed. The advantage of the option (C) is that it can be realized in a one pot synthesis procedure while a two-step procedure is needed for option (B) which, however, allows for better and more precise control of the materials synthesis. Design (B) is needed for devices for which the electronic excitation energy must be transported via FRET to the channel ends, so that it can be transferred to (or interact with) a next object, located at the channel end. Design (C) is a good option, if out-coupling of the electronic excitation energy by luminescence of the J-aggregate is required, as for example in ZeoFRET®-luminescence solar concentrator devices, for which also design (B) can be used. The coupling J-aggregate pair can be covalently linked, if desired.

The photophysical principle is explained in FIG. 5, where we illustrate the energy levels relevant for the situation (B) and (C) reported in FIG. 4, which refers to dyes inside of one channel. It shows the electronic ground state and the electronically excited state of the molecules as solid bars. A dye that has absorbed the energy of a photon is promoted to the excited state. The excitation energy then jumps from one dye to the other, essentially in a random walk process via FRET, until it arrives at the J-aggregate pair where it is captured, because its excited state is of lower energy. The lowering of the excited state energy corresponds to $\beta_c$. Emission from this state occurs with high probability because the oscillator strength of a J-aggregate pair is twice as large as that of the monomer. The photophysical principle is the same for design (B) and design (C). While design (B) allows placing a device at the end of the channels which can capture the excitation energy via FRET very efficiently, this is not possible for design (C). Whether this is of importance or not depends on the application. Advantages that result from this invention with respect to designs that have been invented or known so far are that the chromophore parts of the dyes CHR-spacer and CHR-Davy are structurally the same.

Figure 6:
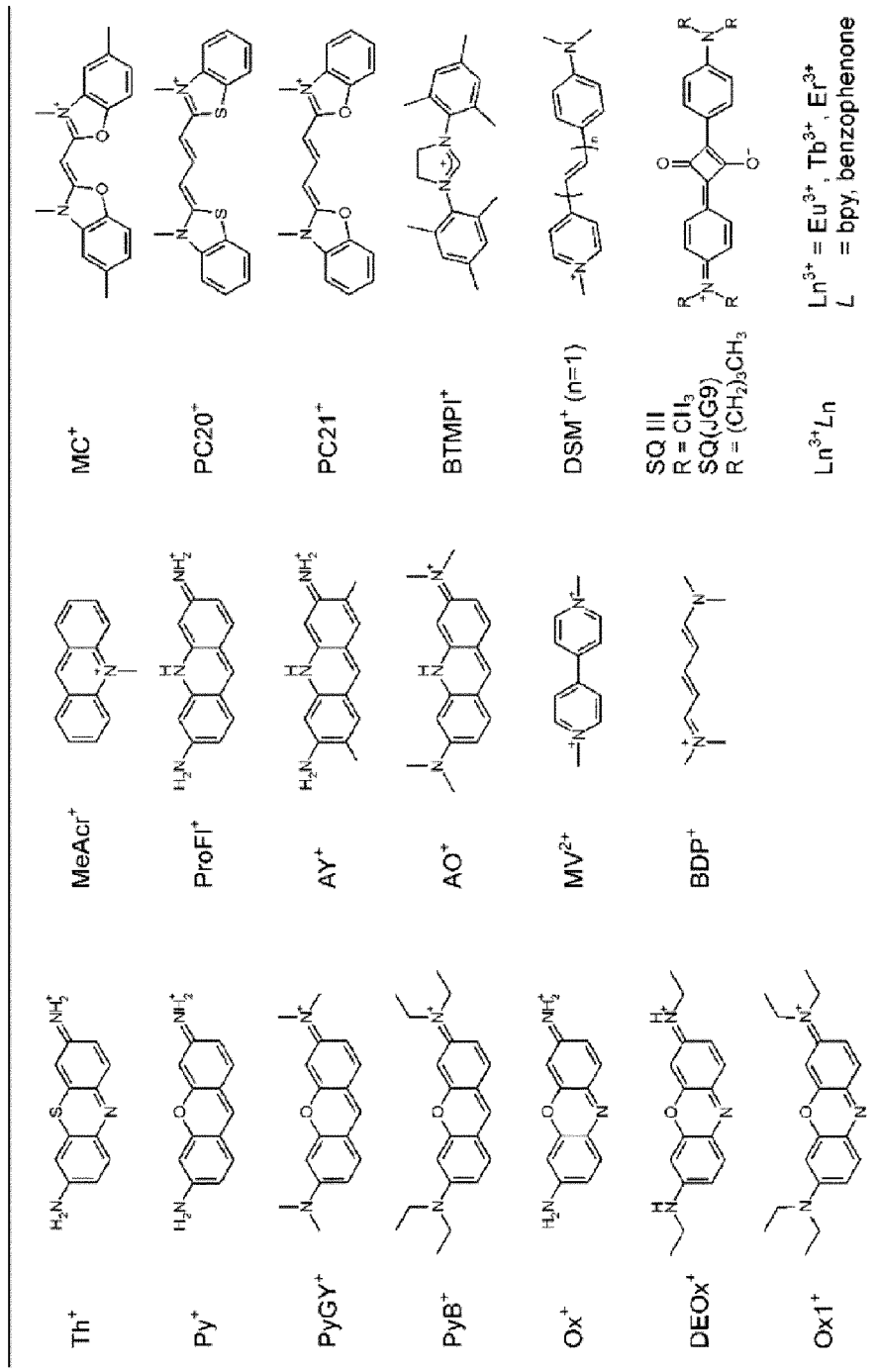
FIG. 6. Examples of cationic dyes that have been inserted in ZL and that are of interest for the discussed applications.
Figure 7:
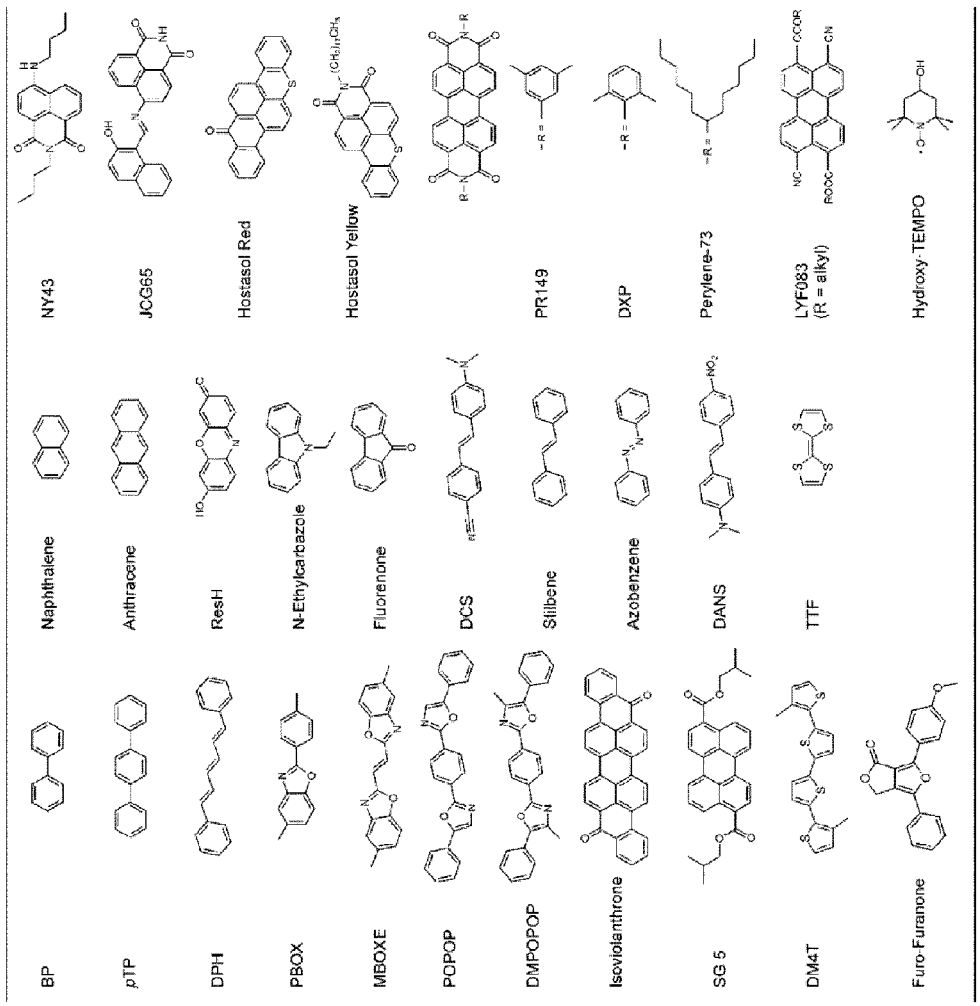
FIG. 7. Examples of neutral dyes that have been inserted in ZL and that are of interest for the discussed applications.

The synthesis of the LJ-ZeoFRET® material is greatly simplified which allows producing it at lower cost. The optical light absorption range of the dyes can be fully exploited. This is especially important for luminescence solar concentrators but also for other applications. While in a conventional antenna material, where the acceptors are different dyes, the absorption range of the acceptors cannot or only partly be used, there is no such limitation for the LJ-ZeoFRET® materials. Imagine that a chromophore is used which absorbs light at wavelengths shorter than 700 nm. In a conventional ZeoFRET® material, an acceptor must be found that absorbs at a wavelength longer than 700 nm. Only small amounts of acceptor can be added, however, since the donor to acceptor ratio should be at least 20 in order to avoid self-absorption, so that the acceptor does not contribute significantly to the light absorption of the ZeoFRET®. The difficulty for realizing this step increases with increasing absorption wavelength range. This is not the case for the LJ-ZeoFRET® materials, because the absorption range of the dyes CHR-spacer and CHR-Davy is identical. Examples of dyes that have been inserted into the channels of ZL and which can be used for preparing ZeoFRET® materials are reported in FIGS. 6 and 7. Among them the perylene, terylene, cyanine, oxazine, bodipy, stilbene, and xanthene dyes are of special importance for the preparation of LJ-ZeoFRET® materials.

EXAMPLES

A typical concept for preparing LJ-ZeoFRET® materials uses two different dyes, one absorbing light at shorter wavelength and the second absorbing light at longer wavelength, a combination of CHR-spacer and CHR-Davy which have the same or nearly the same electronic absorption and luminescence spectra. The light out-coupling is performed by the J-coupling pair consisting of CHR-Davy dyes. Stability can be maximized by selectively plugging the channel entrances by means of a cationic polymer. The chemical and mechanical stability can be further improved by covering the individual particles with a silica layer which can be realized by using standard sol-gel chemistry. This procedure results in non-toxic environmentally friendly materials, independent of the kind of molecules that are inside of the ZL channels. The hexagonal ZL crystals can be assembled in several ways for realizing optically anisotropic layers.

Figure 8:
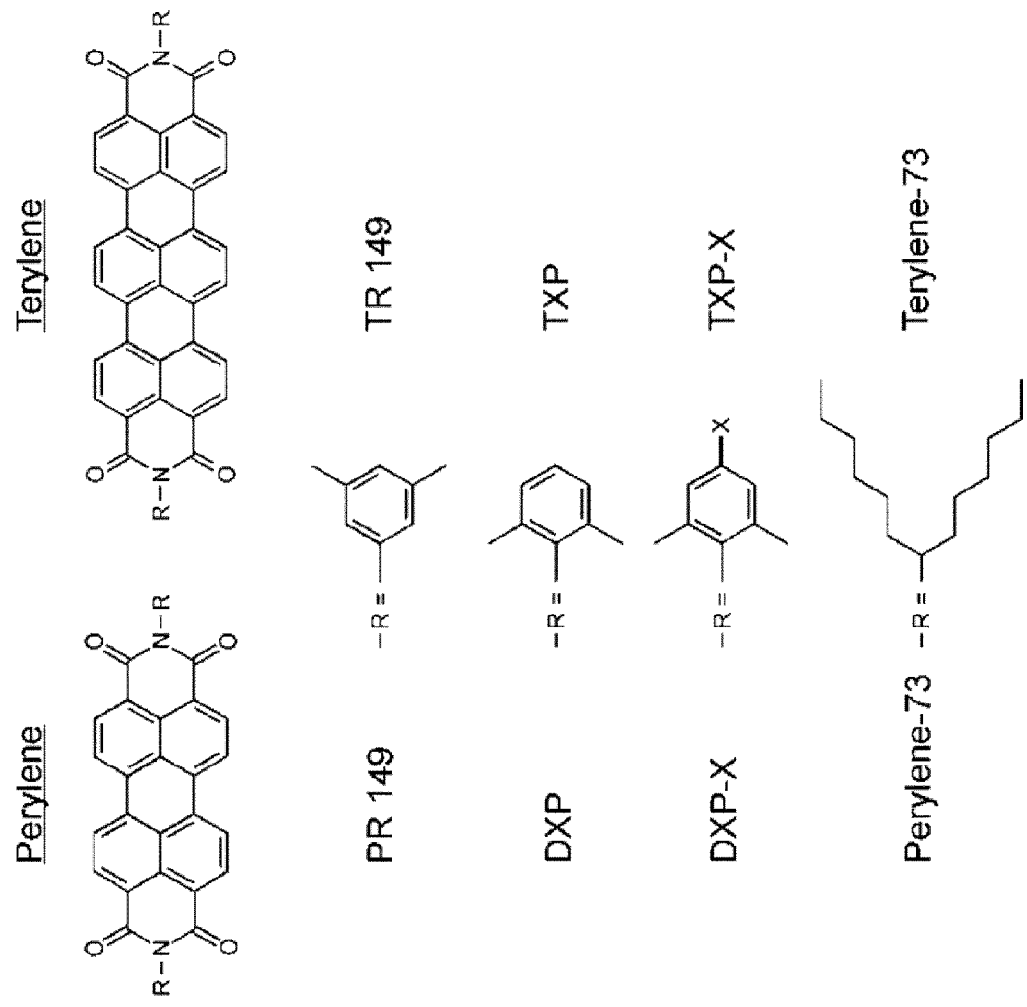
FIG. 8. Examples of perylene and terylene dyes with different distance controlling end groups.
Figure 9:
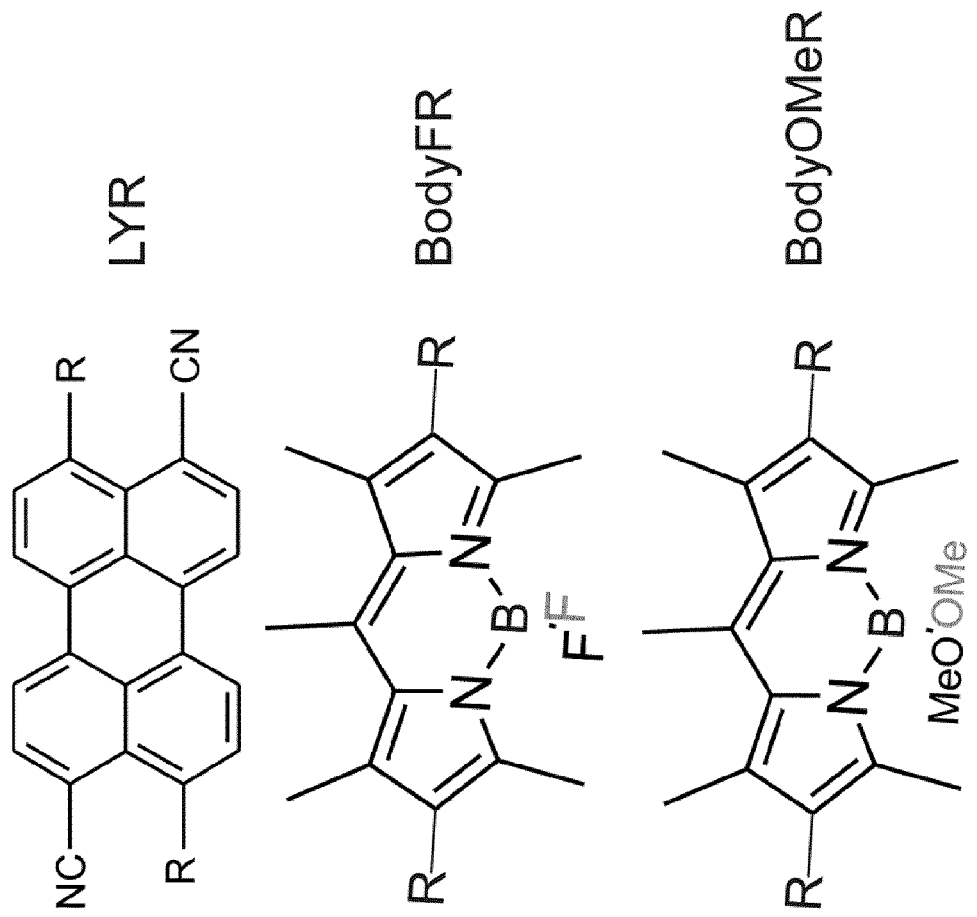
FIG. 9. Further examples of suitable dyes, wherein the distance controlling end groups R have the same meaning as in FIG. 9.

We describe details of the synthesis procedure of a LJ-ZeoFRET® material by using perylene dyes as examples. Examples of perylene dyes with different end groups are shown in FIG. 8 where R and X can be an aliphatic group, a cyclic aliphatic group, an aromatic group, or a combination of both. The aliphatic and the aromatic groups can be substituted in any way needed. They can also be reactive, enabling chemical bonding. The synthesis of such dyes is well known and it has also been known for many years that the electronic absorption and luminescence spectra of these dyes are as a rule not influenced by the end group substituents; here we are interested in these cases and not in the exceptions. (A. Rademacher et al.: Lösliche Perylene-Fluoreszenzfarbstoffe mit hoher Photostabilität, Chem. Ber., 1982, 115, 2927.) The same also holds for terylene dyes (F. O. Holtrup et al.: Terryleneimides: New NIR Fluorescent Dyes, Chem. Eur. J., 1997, 3, 219.) As an example, we use DXP as CHR-Davy molecule. For CHR-spacer we use a molecule with X=phenyl, X=butyl or similar, but also PR149 can be used. We show in FIG. 9 three more examples to illustrate the versatility of this invention. One based on perylene as chromophore, on based on conventional Bodipy and one based on OMe-Bodipy.

Figure 10:
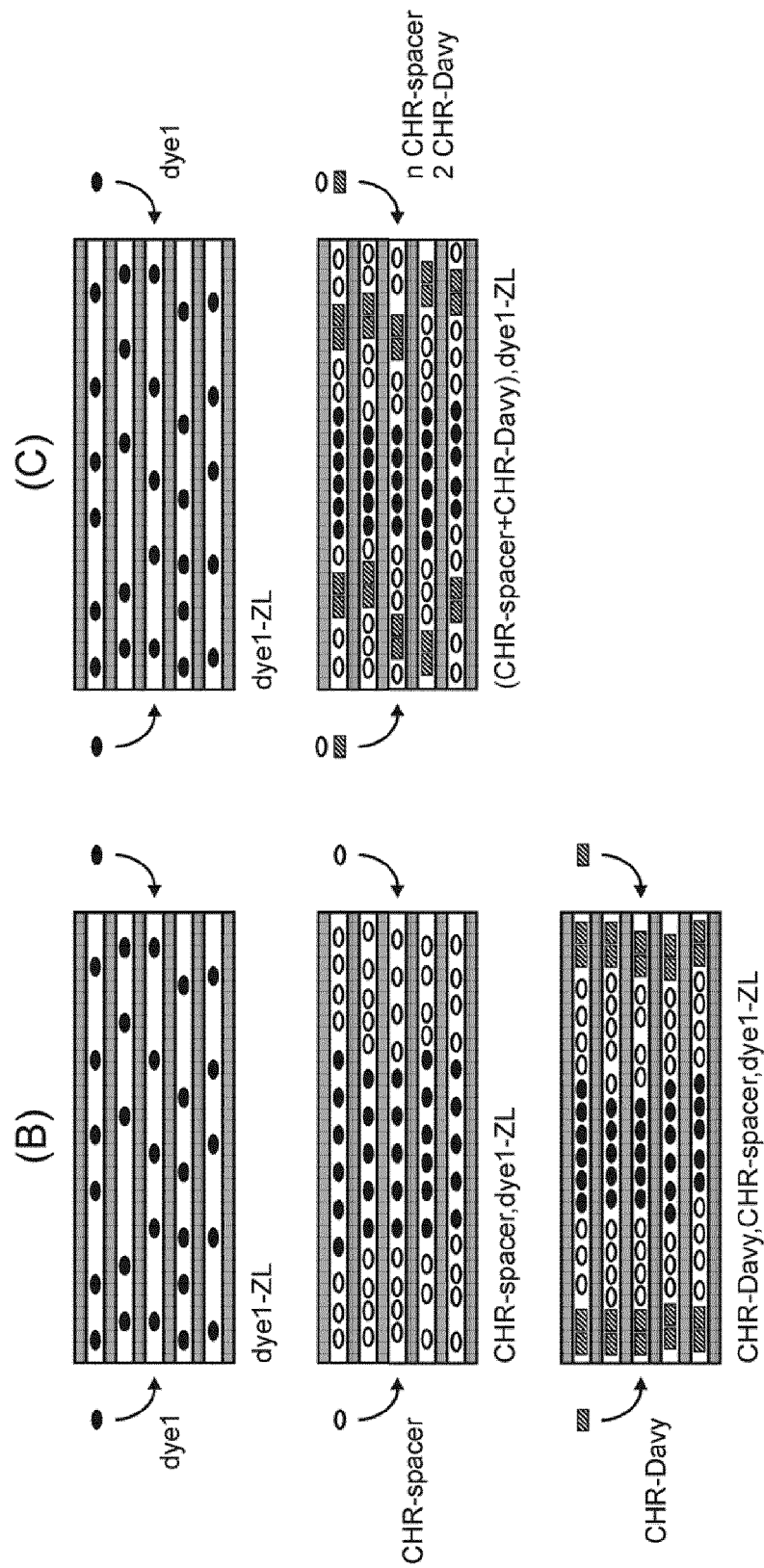
FIG. 10. Synthesis of LJ-ZeoFRET® materials by sequential insertion.

With this, a LJ-ZeoFRET® material according to design (B) and (C) can be synthesized. For both designs, the sequential insertion principle is applied as illustrated in FIG. 10. The sequential insertion principle has been invented by us (M. Pauchard et al.: Dye-Loaded Zeolite L Sandwiches as Artificial Antenna Systems for Light Transport, Chem. Eur. J., 2000, 6, 3456) and has been used successfully for preparing materials such as ZeoFRET®. The fact that this synthesis principle can be used is a prerequisite for the practical realization of our current invention. The procedures for terylene dyes are very similar. The sequential synthesis principle as illustrated in FIG. 10(B) is used to prepare a local LJ-ZeoFRET® material according to design (B). The sequential synthesis principle as illustrated in FIG. 10(C) is applied to synthesize a LJ-ZeoFRET® material according to design (C). A condition that should be fulfilled in this case is that the sublimation temperatures of the CHR-Davy and the CHR-spacer molecules should not be very different. The resulting materials are then used for the applications and in the same way as reported in: CH 698333, WO 2010/009560; EP 18732002, U.S. Pat. No. 7,655,300; WO 2008/052603, PCT/EP2007/005811, CN 1128455; U.S. Pat. No. 7,914,702.

The invention claimed is:

1. A dye loaded zeolite composite material, comprising:
   a plurality of zeolite crystals, each one of said crystals having a proximal face and a distal face opposed therefrom and substantially parallel to said proximal face,
   each one of said crystals having a plurality of straight through uniform channels extending between the proximal face and the distal face and having a channel axis parallel to and a channel width transverse to a longitudinal crystal axis A,
   each channel having a proximal channel end located at the proximal face and a distal channel end located at the distal face, said channels containing a substantially linear arrangement of dye molecules,
   each one of said dye molecules having an elongated shape with a longitudinal extension exceeding a channel width and a lateral extension not exceeding said channel width, and
   said linear arrangement of dye molecules comprising first dye molecules and second dye molecules, each one of said first and second dye molecules consisting of a chromophore moiety arranged between a pair of terminal moieties,
   wherein the chromophore moieties of said first dye molecules and of said second dye molecules are substantially identical, but the terminal moieties of said first dye molecules have a lateral extension larger than half of said channel width so that the terminal moieties of said first dye molecules act as spacer elements and energy can be transported from one to the other of two adjacent first dye molecules via FRET (Foerster resonance energy transfer), while the terminal moieties of said second dye molecules have a lateral extension smaller than half of said channel width so that the terminal moieties of said dye molecules allow for the overlap of the terminal moieties of two adjacent second dye molecules and thus enable J-coupling between these adjacent second dye molecules, and
   said linear arrangement of dye molecules comprises at least one pair of second dye molecules adjacent each other.

2. The dye loaded zeolite composite material according to claim 1, wherein the terminal moieties of said first dye molecules are identical.

3. The dye loaded zeolite composite material according to claim 1, wherein the terminal moieties of said second dye molecules are identical.

4. The dye loaded zeolite composite material according to claim 1, wherein the molar ratio of said first dye molecules to said second dye molecules is at least 20.

5. The dye loaded zeolite composite material according to claim 1, wherein said linear arrangement of dye molecules further comprises third dye molecules, said third dye molecules having an electronic excitation energy that is larger than the electronic excitation energy of said first and second dye molecules.

6. The dye loaded zeolite composite material according to claim 1, wherein said channel ends are provided with closure units.

7. The dye loaded zeolite composite material according to claim 6, wherein said closure units are formed by a plurality of closure molecules having an elongated shape and consisting of a head moiety and a tail moiety, the tail moiety having a longitudinal extension of more than a dimension of crystal unit cells along the longitudinal crystal axis A and the head moiety having a lateral extension that is larger than said channel width and will prevent said head moiety from penetrating into a channel, a channel being terminated, in plug-like manner, at a proximal or distal end thereof, by a closure molecule whose tail moiety penetrates into said channel and whose head moiety substantially occludes said channel end while projecting over said proximal or distal face, respectively.

8. The dye loaded zeolite composite material according to claim 6, wherein said closure units are formed by a closure layer comprising, at one side thereof, a plurality of protruding moieties having a longitudinal extension of more than a dimension of crystal unit cells along the longitudinal crystal axis A and a lateral extension that is smaller than said channel width, each one of said protruding moieties penetrating in plug-like manner the end of an associated channel.

9. The dye loaded zeolite composite material according to claim 8, wherein said closure layer is attached to a solid substrate.

10. A method of producing a dye loaded zeolite composite material according to claim 1, comprising the steps of:
    a) providing an amount of zeolite crystals, each one of said crystals having a pair of substantially parallel faces, each one of said crystals further having a plurality of straight through uniform channels extending between said two faces and having a channel axis parallel to and a channel width transverse to a longitudinal crystal axis A;
    b) either: loading a first amount of first dye molecules into the zeolite channels followed by adding thereto a second amount of second dye molecules, thereby forming a dye loaded zeolite composite material having a terminal acceptor configuration;
    or else: loading a first amount of second dye molecules into the zeolite channels followed by adding thereto a second amount of first dye molecules, thereby forming a dye loaded zeolite composite material having an internal acceptor configuration.

11. The method according to claim 10, further comprising the step, after loading said first dye molecules and said second dye molecules, of closing said zeolite channels.

12. The method according to claim 11, wherein said closing step comprises adding closure molecules having an elongated shape and consisting of a head moiety and a tail moiety, the tail moiety having a longitudinal extension of more than a dimension of crystal unit cells along the longitudinal crystal axis A and the head moiety having a lateral extension that is larger than a channel width and will prevent said head moiety from penetrating into said channel, said channel being terminated, in generally plug-like manner, at the proximal or distal end thereof located at a proximal or distal face of said pair of substantially parallel faces, respectively, by a closure molecule whose tail moiety penetrates into said channel and whose head moiety substantially occludes said proximal or distal channel end while projecting over said proximal or distal face, respectively.

13. The method according to claim 11, wherein said closing step comprises forming a closure layer comprising, at one side thereof, a plurality of protruding moieties having a longitudinal extension of more than a dimension of crystal unit cells along the longitudinal crystal axis A and a lateral extension that is smaller than a channel width, each one of said protruding moieties penetrating in generally plug-ke manner the end of an associated channel.

* * * * *